United States Patent [19]

Cipullo et al.

[11] Patent Number: 5,315,042

[45] Date of Patent: May 24, 1994

[54] USE OF PARTIAL ACETONE CONVERSION FOR CAPACITY INCREASE AND QUALITY/YIELD IMPROVEMENT IN THE BISPHENOL-A REACTION

[75] Inventors: Michael J. Cipullo, Prattville, Ala.; Gaylord M. Kissinger; Isabel M. Matos, both of Evansville, Ind.

[73] Assignee: General Electric Company, Pittsfield, Mass.

[21] Appl. No.: 34,330

[22] Filed: Mar. 22, 1993

[51] Int. Cl.$^5$ .................. C07C 37/20; C07C 39/12
[52] U.S. Cl. .................. 568/727; 568/722; 568/723; 568/728; 568/129
[58] Field of Search ............ 568/727, 722, 728, 724, 568/723; 528/129

[56] References Cited

U.S. PATENT DOCUMENTS

| 2,366,007 | 12/1944 | D'Alello | 568/20 |
| 3,037,052 | 5/1962 | Bortnick | 568/798 |
| 4,822,923 | 4/1989 | Li | 568/724 |
| 4,859,803 | 8/1989 | Shaw | 568/727 |
| 4,876,391 | 10/1989 | Kissinger | 568/724 |
| 4,902,836 | 2/1990 | Kissinger | 568/702 |
| 4,918,245 | 4/1990 | Iimura et al. | 568/727 |

OTHER PUBLICATIONS

Encyclopedia of Polymer Science and Technology, 1967, vol. 7, pp. 695-708 and third edition, 1981.

Primary Examiner—Werren B. Lone

[57] ABSTRACT

Product quality productivity of continuous bisphenol-A (BPA) are increased by increasing the flow rate of reactants through the reactor and decreasing % acetone conversion in the presence of an ion exchange resin catalyst and an optional free mercaptan promoter.

26 Claims, 1 Drawing Sheet

USE OF PARTIAL ACETONE CONVERSION FOR CAPACITY INCREASE AND QUALITY/YIELD IMPROVEMENT IN THE BISPHENOL-A REACTION

BACKGROUND OF THE INVENTION

Bisphenol-A (BPA) is prepared by the reaction of phenol and acetone in the presence of an acidic catalyst, such as HCl or an ion exchange resin. During the reaction, a number of unwanted by-products and color are formed which affect yield and quality. The formation of such by-products and color is related to acetone concentration, retention time and temperature in the reactor. Some of the by-products are precursors of other impurities which can be formed in the various purification steps (distillations, crystallizations, etc.) used to produce the desired final product quality.

Typically, the BPA reaction is run in such a way that all the acetone in the reactor feed stream is consumed till depletion to achieve the desired capacity. This results in high retention times With the subsequent formation of extra by-products. It is desired to reduce the retention time, the resulting unwanted by-products and minimize the color effects.

SUMMARY OF THE INVENTION

The present invention is based upon the discovery that by increasing the throughput of the reactor, and taking advantage of high reaction rates in the beginning of the reaction (high acetone in the beginning versus the end), retention time in the reactor is reduced and a higher productivity per reactor is achieved. Also, a shift in by-products distribution occurs resulting in a reduction of non-isomerizables and therefore better quality and yield.

In one embodiment, the invention is directed to a continuous process for the preparation of bisphenol-A (BPA) comprising the steps of contacting phenol and acetone in the presence of an acidic catalyst at a selected relatively high effluent stream flow rate sufficient to result in a decrease in acetone conversion and an initial increase in BPA production; and removing formed BPA and added acetone from the effluent stream after formation of BPA and prior to depletion of the acetone.

DESCRIPTION OF THE INVENTION

Figure 1:
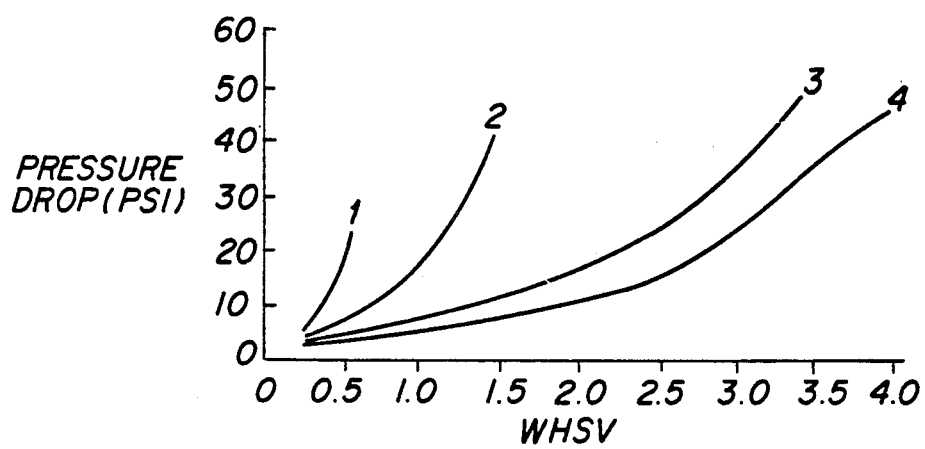
FIG. 1 is a graphical representation of the pressure drop versus the weighted hourly space velocity (lbs reactor feed/hr/lbs dry catalyst) (WHSV) in a reactor used to evaluate the present invention.

In accordance with the present invention, bisphenol-A (BPA) is continuously prepared by a reaction of phenol and acetone in the presence of an acidic catalyst under accelerated flow conditions or increased throughput such that initial production of BPA is increased. The acetone and BPA are separated from the effluent stream prior to depletion of the acetone whereby the residence time of the BPA is reduced and undesirable by-products and color are reduced.

In one embodiment, phenol and acetone are contacted in the presence of an acidic catalyst at a relatively high effluent stream rate to promote an increase in initial production of BPA and a decrease in acetone conversion, sometimes referred to hereinafter as partial acetone conversion. The BPA is then separated from the acetone in the effluent stream prior to depletion of the acetone and the separated acetone is then recycled.

Although any acid catalyst system can be employed it is much preferred to employ a solid acid catalyst system so that there are no unnecessary separation steps of one liquid from another or acid recovery steps. Such acid catalyst systems are commonly present as organic acid catalyst systems such as the sulfonic acid cation exchange resins manufactured by various companies. Examples of acidic ion exchange resins useful in catalyzing this reaction are generally well known compositions as are methods of their preparation, see for example the preparative procedures described in U.S. Pat. No. 3,037,052 which is hereby incorporated herein by reference thereto. Representative of acid ion-exchange resins are strong-acid ion exchangers, such as those resins or polymers having a plurality of pendant sulfonic acid groups. Examples include sulfonated polystyrene or poly(styrenedivinylbenzene) copolymer and sulfonated phenolformaldehyde resins. The sulfonated resins are commercially available in water swollen form as gelular and macro-reticular types. Specific examples of commercially available resins are Amberlite IR-120H, Amberlyst 15H, Amberlyst 31, Dowex 50-X-4, Dowex MSC-LH, Duolite c-291, (Amberlite, Amberlyst, Dowex and Duolite, are registered U.S. trademarks). Further examples of such ion exchangers as well as methods for preparing such ion exchangers are described in the Encyclopedia of Polymer Science and Technology, 1967, vol. 7, pages 695 to 708 and third edition, 1981. The exchange capacity of the acidic resin is preferably at least 2.0 meq. H+/g of dry resin, with exchange capacities in the range of from 3.0 to 5.5 meg. H+/g (dry resin) particularly preferred. Preferred catalysts are the Amberlyst® gelular types, which are styrene cross-linked with divinylvenzene or like cross-linking monomer and having pendant sulfonic acid groups attached to the aromatic nucleus of the styrene moiety. Sulfonation may be by the process described in U.S. Pat. No. 2,366,007 which is incorporated herein by reference thereto. See also U.S. Pat. Nos. 4,902,836 and 4,876,391 incorporated herein by reference.

Preferred catalyst systems include a cation exchange resin such as Rohm and Haas XE-364, also known as Amberlyst 31. This resin is a sulfonated polystyrene. Either a single reactor or multiple reactors in series can be used.

The following examples illustrate the benefits of the partial acetone conversion process of the invention but should not be considered a limitation thereon.

The data summarized in Tables 1, 2 and 3 was obtained on a small scale with reactors containing approximately 2960 pounds (dry basis) of a stationary catalyst resin. The preferred immobilized catalysts herein are sulfonated ion exchange catalysts incorporated into a polystyrene backbone cross-linked with a suitable cross-linking agent and a divinyl benzene. In the examples below, resins containing about 2% Cross-linking (e.g. Mobay Lewatit, or Rohm & Haas XE561) and about 4% cross-linking (e.g. Rohm and Haas XE-364, or Amberlyst 31) were used. The reactors were jacketed flow through stainless steel vessels (about 5'6", internal diameter and 5' internal height) with the Jacket temperature maintained at about 167° F. via a closed loop tempered water system. The bottoms contained a sand bed and Johnson screens to prevent escape of the resin. After removing the majority of the BPA from the effluent stream, the mother liquor was returned to the reactor feed, with additional acetone and phenol to make up for losses of material converted to para-para-bisphenol-A (pp-BPA). An optional free or mobile mercaptan promoter (3-mercaptopropionic acid) was also present in the stream.

Differences in the % acetone conversion between Tables 1 and 2 show the effect of the catalyst cross-linking on the process. The higher cross-linked resin used in Table 2 appears to have slowed down the reaction rate slightly relative to the lower cross-linked resin (Table 1). The higher rigidity of the higher cross-linked resin allows reactants to pass at higher flows through the bed, thus increasing productivity while minimizing bead compression. The result is a minimization of pressure drops across the bed.

Table 3 illustrates the effects of process variables on productivity. The data shows that increasing acetone concentration in the reactor feed from 4.2% (wt) to

TABLE 1

Effect of Flow Rate on pp-BPA Production Rate and Quality (2% cross-linked resin)

| WHSV | GPM | % Acetone Conversion | pp-BPA Content | pp-BPA #/min. | PHENOL FREE COMPOSITION | | | 350 nm* Color |
|---|---|---|---|---|---|---|---|---|
| | | | | | pp-BPA | op-BPA | Dimers | |
| 0.25 | 1.43 | 97 | 23.7 | 2.7 | 97 | 1.8 | 0.4+ | 13.7 |
| 1.0 | 5.7 | 91 | 22.3 | 10.1 | 96 | 2.9 | 0.3 | 11.9 |
| 1.5 | 8.6 | 78 | 21.5 | 14.8 | 96 | 2.7 | 0.1 | 10.2 |

TABLE 2

Effect of Flow Rate on pp-BPA Production Rate and Quality (4% cross-linked resin)

| WHSV | GPM | % Acetone Conversion | pp-BPA Content | pp-BPA #/min. | PHENOL FREE COMPOSITION | | | 350 nm* Color |
|---|---|---|---|---|---|---|---|---|
| | | | | | pp-BPA | op-BPA | Dimers | |
| 0.25 | 1.43 | 96 | 23.6 | 2.7 | 94.7 | 2.4 | 1.3 | 16.7 |
| 1.0 | 5.7 | 83 | 22.2 | 10.0 | 96.3 | 3.7 | 0.5 | 10.4 |
| 1.5 | 8.6 | 71 | 21.2 | 14.4 | 96.9 | 2.8 | 0.1 | 10.3 |

TABLE 3

Effect of Increased Acetone and Promoter

| WHSV | GPM | ppm 3 MPA | feed % Acetone | % Acetone Conversion | pp-BPA Content | pp-BPA #/min | 350 nm* Color | delta** 350 nm Color |
|---|---|---|---|---|---|---|---|---|
| 1.5 | 8.6 | 400 | 4.2 | 78% | 21.5 | 14.8 | 10.2 | 0.9 |
| 1.5 | 8.6 | 400 | 6.0 | 67% | 24.2 | 16.6 | 11.2 | 2.2 |
| 1.5 | 8.6 | 2000 | 6.0 | 83% | 27.7 | 19.1 | 11.7 | 2.8 |

*350 nm Color refers to UV-VIS absorbance value of 0.5 gram sample dissolved in 50 ml Methanol (X100) measured spectroscopically.
**delta 350 nm color refers to increase in the color of the solution as it is passed through the reactor where BPA and by-products are formed (350 nm color of outlet minus 350 NM color of inlet).

Tables 1 and 2 show the effect of increased flow rate on effluent composition, color and pp-BPA production rate. In each case, the feed contains the recycle stream after removing the majority of pp-BPA (except about 8–11% pp-BPA), and 4.2% (wt) added acetone. As the flow is increased, the weight percent of the acetone which is consumed decreases, the stream color decreases, and the pp-BPA production rate increases. In addition, the amount of non-isomerizable products (e.g. dimer) decreases and the amount of isomerizable products [e.g. ortho-para-bisphenol-A (op-BPA)] increases slightly with increasing flow rate. The isomerizable products eventually convert back to pp-BPA at a later point in the pp-BPA production process, and are therefore not a serious concern. The non-isomerizable products, i.e. dimers, are unwanted, however, because they are considered unrecoverable and represent a yield loss. The amount of color in the reactor effluent decreases with increasing flow rate. The above changes in composition and color are all desirable effects and illustrate the advantage of the faster partial acetone conversion conditions of the invention.

6.0% gives a reduction in the percent of the acetone which is consumed (e.g. 6.0% in feed and 1.0% in effluent $=(6-1)/6=83\%$ acetone conversion). While the percent of acetone consumed decreases, the overall productivity of the system (pounds of BPA produced per minute) increases. The unreacted acetone is easily recovered from the reaction effluent by distillation and recycled to the reactor because it is the lowest boiling component. A slight increase in by-products is seen when the feed % acetone is increased with all other variables constant.

Table 3 also shows the effect of the optional free mercaptan promoter concentration, i.e. 3-mercaptopropionic acid (3-MPA) on % acetone conversion and productivity. Increased promoter results in increased acetone conversion and increased productivity. Other mercaptan promoters such as ethyl or methyl or propyl mercaptan may also be useful. A small reduction in the amount of impurities is also observed per amount of pp-BPA formed.

The catalyst bead size and % cross-linking also influences the operating conditions of the system. In the examples, the percent cross-linking refers to the weight percent of a cross-linking agent (e.g. divinyl benzene) that was incorporated into the polystyrene backbone of the exemplary sulfonated ion exchange catalyst when it was manufactured. Catalyst resins with various cross-linking contents are available from many commercial suppliers and often range from 2% to 8% or higher. Smaller bead size results in increased pressure drop across the bed as shown in Table 4 below.

TABLE 4

Effect of Catalyst Bead Size on Pressure Drop
(2% cross-linked resin, similar reaction conditions:
4.2% acetone in feed)

| Average Bead Diameter (dry, mm) | PSI Pressure Drop (12' bed height) | Flux Rate Gallons/ft²/min |
|---|---|---|
| 0.4 mm | 15-20 psi | 0.2 |
| 0.5 mm | 12-16 psi | 0.2 |

Increased cross-linking results in reduced pressure drop as the beads are more rigid and do not flex or change shape as readily under conditions of high flow. Lower cross-linked beads tend to deform under load, filling the void spaces and increasing pressure drop. FIG. 1 depicts the relationship between pressure drop (psi) and the weighted hourly space velocity (WHSV). The data illustrates the effect of catalyst cross-linking and bed height on pressure drop. This data was obtained in a cylindrical vessel to investigate pressure drop under a variety of reaction conditions: bed heights, flow rates, feed compositions.

For example, curves 1 and 2 represent pressure drop (psi) as a function of the weighted hourly space velocity (WHSV) (e.g., lbs reactor feed/hr/lbs dry catalyst) of the effluent through a 2% cross-linked ion exchange resin. Curve 1 represents a 12' bed height and curve 2 represents a 9' bed height. Curves 3 and 4 represent psi v. WHSV in a 4% crosslinked ion exchange resin at bed heights of 12' and 9', respectively. The higher cross-linked catalyst promotes higher flow rates, because the increased cross-linking increases the resistance of the catalyst to deformation and hence decreases catalyst compression under pressure.

The pressure drop ($\Delta P$), which is a measure of the resistance to flow, increases with increased bed height. Alternatively, $\Delta P$ increases with increasing WHSV. Using FIG. 1 as a guide, a 2% cross-linked catalyst in a 12' bed height would have an excessive $\Delta P$ as WHSV is increased above about 0.5. Thus, relative BPA production would not be greatly increased with increasing flow rate because the pressure drop would limit the throughput of the reactants. Conversely, if the bed height is reduced to 9', a desirable increase in WHSV (e.g., 1) can be readily achieved without an excessive $\Delta P$, e.g., >25psi. At a WHSV of 1.5, $\Delta P$ exceeds 25 psi. If a 4% cross-linked catalyst is employed, a WHSV between 1 and 2 can be readily achieved without an excessive pressure drop. As a practical expedient, a $\Delta P$ of not more than about 25 psi is desired using currently available equipment. Higher pressure drops can be accommodated if desired. However, the equipment may require modification to achieve such higher pressures.

Figure 2:
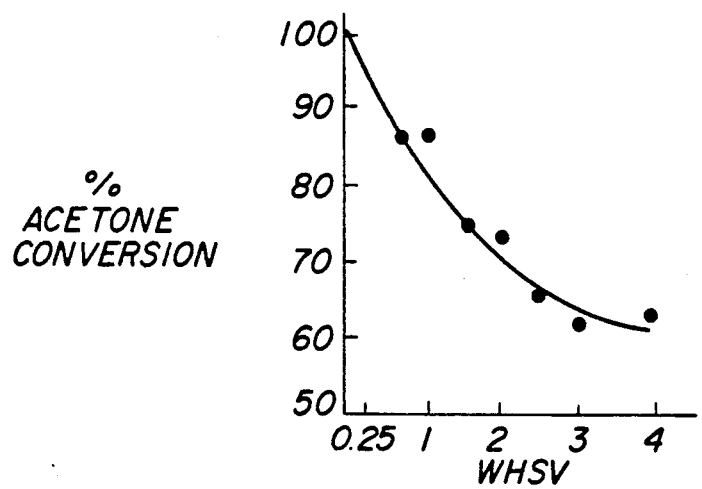
FIG. 2 is a graphical representation of acetone conversion versus WHSV in a reactor used to evaluate the present invention.
Figure 3:
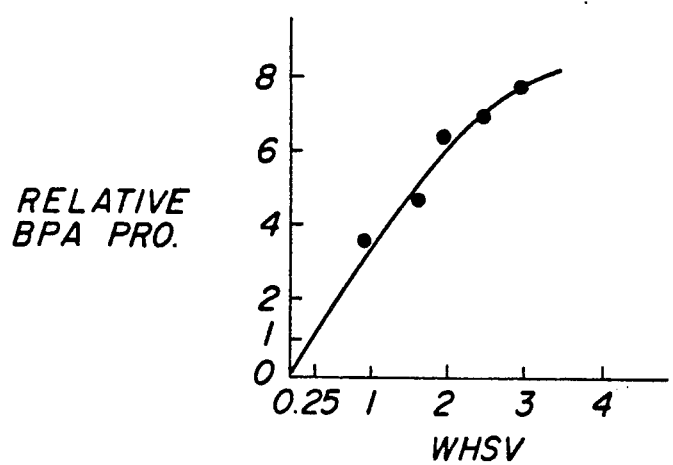
FIG. 3 is a graphical representation of relative productivity versus WHSV in a reactor used to evaluate the present invention.

FIG. 2 shows % acetone conversion versus WHSV. FIG. 3 shows relative productivity, where the quantity of BPA produced is 1.0 at WHSV=0.25. In both figures, a 4% cross-linked ion exchange resin catalyst is used. Cross-linking up to about 8% is useful. Higher cross-linking is possible and may be employed in applications where less bed compression and lower flow resistance are desired.

Acetone conversion decreases with increased flow rate while productivity increases dramatically. The effect is that higher production of BPA may be achieved with increased flow through the same size vessel (or the vessel size may be reduced while maintaining the same flow rate). The relative productivity increases for incremental increases in WHSV. The % acetone conversion decreases for a corresponding increase in WHSV.

As can be appreciated from FIGS. 2 and 3, acetone conversion decreases with increased flow rate as characterized by WHSV; and relative BPA production increases with flow rate also characterized by WHSV. The curves in FIGS. 2 and 3 are respectively decreasing or increasing to a limit. In FIG. 3, the relative BPA production increases with incremental changes in WHSV. For example, current processes, operating at a WHSV of 0.25, results in a relative BPA production of 1. At a WHSV of 1, relative BPA production is about 3.8. This means that increasing the throughput by a factor of four results in a slightly lesser increase in production without requiring any equipment modifications. The data shows results for an increase in relative BPA production as WHSV is increased to about 4. Theoretically, WHSV may be increased to any level. However, as a practical consideration, as WHSV approaches about 4, the advantages resulting from increased BPA production is balanced by the disadvantages of handling such a larger throughput. Accordingly, the throughput should be limited to a WHSV of about 4 using the same equipment. Preferably, the invention advantageously operates at a WHSV in the range from about 1 to about 2.

In summary, the design of a highly efficient pp-BPA ion exchange resin reaction system requires selection of a catalyst system (e.g. % cross-linking), selection of appropriate reaction vessel geometry which minimizes pressure drop by relating bed height to flow, bead size, selection of concentrations of an appropriate free mercaptan promoter and acetone, and proper choice of space velocity (WHSV, flow rate versus bed volume of catalyst used, i.e., residence time). With the proper selection of reaction conditions, high production rates can be achieved while minimizing by-product and color formation.

While there has been described what at present are considered to be the preferred embodiments of the present invention, it will be readily apparent to those skilled in the art that various changes and modifications may be made therein without departing from the invention and it is intended in the appended claims to cover such changes and modifications as fall within the true spirit and scope of the invention.

We claim:
1. A method for the continuous production of bisphenol-A comprising the steps of:
   contacting phenol and acetone in the presence of an acidic catalyst at an accelerated flow rate through the catalyst, said flow rate being sufficient to result in a decrease in acetone conversion, whereby the proportion of acetone is maintained at a high level resulting in a high reaction rate and a corresponding increase in bisphenol-A production; and a corresponding separating formed bisphenol-A and prior to depletion of the acetone whereby the resi- dence time of the bisphenol-A is reduced and undesirable by products and color are reduced.

2. The method according to claim 1, wherein the flow rate through the catalyst is greater than a weighted hourly spaced velocity (WHSV) of about 0.25.

3. The method according to claim 2, wherein the weighted hourly space velocity is in a range from about 0.25 to about 4.

4. The method according to claim 2, wherein the weighted hourly space velocity is in a range from about 1 to about 2.

5. The method according to claim 2, wherein the decrease in acetone conversion is up to about 40% at a weighted hourly space velocity of 4.

6. The method according to claim 1, wherein the relative increase in bisphenol-A production is up to about 8 fold at a weighted hourly space velocity of 4.

7. The method according to claim 1, further comprising adding an effective amount of a mercaptan promoter for increasing acetone conversion.

8. The method according to claim 1, wherein the catalyst comprises a stationary ion exchange resin.

9. The method according to claim 8, wherein the resin contains at least 2% cross-linking.

10. The method according to claim 8, wherein the resin contains cross-linking in a range from about 2% to about 8%.

11. The method according to claim 1, further comprising adding a free mercaptan promoter in the feed stream for increasing % acetone conversion.

12. The method according to claim 1, wherein the UV-VIS absorbance of a 0.5 gram sample of bisphenol-A dissolved in 50 ml. methanol is reduced as throughput is increased.

13. The method according to claim 1, wherein production of undesirable byproducts is reduced as the throughput of the reactants is increased.

14. The method according to claim 1, wherein the flow rate through the catalyst results in a pressure drop across the catalyst up to about 25 psi.

15. A method for the continuous production of bisphenol-A comprising the steps of contacting a stream of phenol and acetone in the presence of a stationary acidic catalyst and a free mercaptan promoter at an increased flow rate of the stream through the catalyst above a weighted hourly space velocity of about 0.25 whereby the reaction rate is maintained at a higher level and bisphenol-A production is increased and separating bisphenol-A from the stream after formation of the bisphenol-A and prior to consumption of the acetone substantially to depletion whereby the residence time of the bisphenol-A is reduced and undesirable by-products and color are reduced.

16. The method according to claim 15, wherein the mercaptan promoter comprises a compound selected from the group consisting of:
3-mercaptopropionic acid ethyl, methyl and propyl mercaptan.

17. The method according to claim 15, wherein the 3-mercaptopropionic acid is present in an amount up to 2,000 ppm of effluent.

18. The method according to claim 15, wherein the weighted hourly space velocity varies in a range from about 0.25 to about 4.

19. The method according to claim 15, wherein the weighted hourly space velocity varies in a range from about 1 to about 2.

20. The method according to claim 15, wherein the UV-VIS absorbance of a 0.5 gram sample of bisphenol-A dissolved in 50 ml. methanol is reduced as throughput is increased.

21. The method according to claim 15, wherein the production of bisphenol-A increases with an incremental increase in effluent flow rate.

22. The method according to claim 15, wherein the acetone conversion decreases with increasing effluent flow rate.

23. The method according to claim 15, wherein production of undesirable byproducts is reduced as the throughput of the reactants is increased.

24. The method according to claim 15, wherein the acetone conversion varies in a range from about 97% to about 60% for a corresponding variation in weighted hourly space velocity from about 0.25 to about 4.

25. The method according to claim 15, wherein the relative production of bisphenol-A varies in a range from about 1 to about 8 fold for a corresponding variation of weighted hourly space velocity from about 0.25 to about 4.

26. The method according to claim 15, wherein the flow rate through the catalyst results in a pressure drop across the catalyst of up to about 25 psi.

* * * * *